(12) United States Patent
Holmqvist

(10) Patent No.: US 10,166,341 B2
(45) Date of Patent: Jan. 1, 2019

(54) MEDICAMENT DELIVERY DEVICE

(71) Applicant: Carebay Europe Ltd, Swatar (MT)

(72) Inventor: Anders Holmqvist, Värmdö (SE)

(73) Assignee: Carebay Europe Ltd, Sliema (MT)

( * ) Notice: Subject to any disclaimer, the term of this patent is extended or adjusted under 35 U.S.C. 154(b) by 793 days.

(21) Appl. No.: 14/412,613

(22) PCT Filed: Jun. 12, 2013

(86) PCT No.: PCT/EP2013/062081
§ 371 (c)(1),
(2) Date: Jan. 2, 2015

(87) PCT Pub. No.: WO2014/005807
PCT Pub. Date: Jan. 9, 2014

(65) Prior Publication Data
US 2015/0190582 A1    Jul. 9, 2015

Related U.S. Application Data

(60) Provisional application No. 61/669,023, filed on Jul. 7, 2012.

(30) Foreign Application Priority Data

Jul. 6, 2012  (SE) ..................... 1250789

(51) Int. Cl.
*A61M 5/315* (2006.01)
*A61M 5/24* (2006.01)

(52) U.S. Cl.
CPC .......... *A61M 5/31535* (2013.01); *A61M 5/24* (2013.01); *A61M 5/31525* (2013.01);
(Continued)

(58) Field of Classification Search
CPC .......... A61M 5/31535; A61M 5/31553; A61M 2005/2407; A61M 5/24; A61M 5/31525; A61M 5/31543; A61M 5/31585
See application file for complete search history.

(56) References Cited

U.S. PATENT DOCUMENTS

| 5,226,896 A * | 7/1993 | Harris ............... A61M 5/31551 604/208 |
| 5,925,021 A | 7/1999 | Castellano et al. |
| 2006/0153693 A1 | 7/2006 | Fiechter et al. |

FOREIGN PATENT DOCUMENTS

| EP | 0554996 A1 | 8/1993 |
| WO | 2004/002556 A1 | 1/2004 |

(Continued)

OTHER PUBLICATIONS

EPO, Int'l Search Report in PCT/EP2013/062081, dated Oct. 10, 2013.
EPO, Written Opinion in PCT/EP2013/062081, dated Oct. 10, 2013.

*Primary Examiner* — Bhisma Mehta
*Assistant Examiner* — Brandy S Lee
(74) *Attorney, Agent, or Firm* — Piedmont Intellecutual Property

(57) ABSTRACT

The invention relates to a medicament delivery device (100) having a a drive mechanism arranged to drive a plunger rod (12). A release button (4) is movable between an active and an inactive state, wherein the release button (4) in the active state allows the actuator (3) to move axially towards a proximal end position and wherein the release button (4) in the inactive state allows the actuator (3) can move axially towards the proximal end position or towards the distal end position.

16 Claims, 6 Drawing Sheets

(52) U.S. Cl.
CPC .... *A61M 5/31553* (2013.01); *A61M 5/31585* (2013.01); *A61M 5/31543* (2013.01); *A61M 2005/2407* (2013.01)

(56) References Cited

FOREIGN PATENT DOCUMENTS

| | | |
|---|---|---|
| WO | 2007/017052 A1 | 2/2007 |
| WO | 2009/092807 A1 | 7/2009 |
| WO | 2010/115670 A1 | 10/2010 |
| WO | WO2010115670 * | 10/2010 |
| WO | 2010/139643 A1 | 12/2010 |
| WO | 2011/089246 A1 | 7/2011 |
| WO | 2014/005808 A1 | 1/2014 |

\* cited by examiner

MEDICAMENT DELIVERY DEVICE

FIELD OF THE INVENTION

The present invention relates to a medicament delivery device, especially a multi-dose reusable injection device.

BACKGROUND OF THE INVENTION

Reusable injection devices which can be reloaded with a new medicament container when a prior medicament container is emptied are known in prior art. For example, pen injectors for insulin are commonly known. WO-2004/002556 discloses a re-usable pen injector for use with medicament containers, comprising a drive mechanism having a plunger rod acting on a plunger in the container and when the container has been emptied to a pre-defined extent, the plunger rod can be reset to an initial position by unscrewing the two housing parts.

SUMMARY OF THE INVENTION

It is an object of the invention to provide a medicament delivery device with improved user friendliness and reliability in operation. This object and other objects are solved by a medicament delivery device as defined in claim 1. Preferred embodiments of the present invention are defined in the dependent claims.

Thus, in accordance with an aspect of the present invention, there is provided a medicament delivery device having a proximal end and a distal end, said medicament delivery device comprising a front housing and a rear housing interconnected and axially displaceable relative to each other between an extended position and a retracted position. A plunger rod is arranged to act on a plunger of a medicament container held in the medicament delivery device and a drive mechanism is arranged to drive said plunger rod. An actuator is connected to the front and rear housings respectively and is axially movable in said front and rear housings between a proximal end position and a distal end position and the actuator is biased by a first biasing element towards said distal end position. A drive sleeve is releasably connected to said actuator and arranged to act on said drive mechanism for driving said plunger rod. Further, a locking ring is rotatably arranged at a distal end of the rear housing and in threaded connection with an outer surface of the actuator, wherein the locking ring is prevented from axial movement relative to the rear housing. A release button is arranged on the rear housing and movable between an active and an inactive state. The release button, in said active state, allows unidirectional rotational movement of the locking ring relative to the rear housing such that the actuator can move axially towards said proximal end position under rotational movement of the locking ring and, in said inactive state, allows bidirectional rotational movement of the locking ring relative to the rear housing such that the actuator can move axially towards said proximal end position or towards said distal end position under rotational movement of the locking ring.

If a user of a previously known medicament delivery device, for some reason, would let go of the actuator during injection of a medicament, i.e. before the complete dose has been injected, the actuator would return to its distal end position and the user would have to estimate how much of the dose that still had to be injected to achieve the intended dose. This leads to a great amount of uncertainty and may even endanger the health of the user. The provision of the unidirectionally rotatable locking ring to the medicament delivery device according to the present invention allows a user to press the actuator towards the proximal end position in steps and the actuator will not move towards its distal end position if the user releases the actuator before the complete dose is injected. This makes the medicament delivery device according to the present invention more user friendly than prior art devices and increases safety since a user can always be certain that the intended dose is injected as soon as the actuator is completely depressed from the distal end position to the proximal end position independent of how the actuator is depressed, i.e. continuously or in steps.

In accordance with an embodiment of the medicament delivery device according to the invention, the front housing and the rear housing are interconnected and axially displaceable relative to each other by means of an outer thread on the front housing and an inner thread on the rear housing.

The provision of mutually corresponding inner and outer threads ensures a reliable connection between the front and the rear housings which allows a high degree of accuracy during adjustment.

In accordance with an embodiment of the medicament delivery device according to the invention, the drive sleeve is biased towards a distal end of the medicament delivery device by means of a second biasing element.

By providing a second biasing element, reliability of the device can be further enhanced.

In accordance with an embodiment of the medicament delivery device according to the invention, an outer surface of the actuator is provided with dose indicators and wherein the locking ring has a dose window through which said dose indicators can be seen.

This is a simple and reliable way of presenting a set dose and allows the user to immediately realize the currently set dose.

In accordance with an embodiment of the medicament delivery device according to the invention, the dose ring is held axially immovable relative to said rear housing by means of a transparent dose ring cover.

By providing a transparent dose ring cover to the rear end of the rear housing, axial immovability of the dose ring is guaranteed while still providing excellent visibility of the set dose.

In accordance with an embodiment of the medicament delivery device according to the invention, the drive mechanism comprises a drive nut fixedly arranged near a proximal end of said front housing and wherein the drive nut comprises a through-bore, a part of which is provided with an inner thread. A proximal end of a hollow drive rod having an outer thread is unidirectionally rotatably mounted to said drive nut. A plunger rod is arranged within said hollow drive rod and in threaded connection with the inner thread of the bore of the drive nut and the plunger rod and the hollow drive rod are arranged to mate with each other such that axial movement of the plunger rod relative to the hollow drive rod is allowed while rotation of said plunger rod relative to the hollow drive rod is prevented. The drive sleeve, in turn, is arranged in threaded connection with the outer thread of said hollow drive rod.

This arrangement will convert the linear movement of the drive sleeve into a rotational movement of the hollow drive rod and the plunger rod which will then also rotate due to the fact that it is prevented from rotation relative to the hollow drive rod. The plunger rod, being in threaded connection with the inner thread of the bore of the drive nut, will be driven axially forward towards a proximal end of the medicament delivery device when the plunger rod rotates, thus forcing the plunger of a medicament container held in the medicament delivery device forwardly.

In accordance with an embodiment of the medicament delivery device according to the invention, the drive sleeve is arranged within and axially movable relative to the actuator and wherein coupling means are arranged to prevent the drive sleeve and the actuator from rotational movement relative to each other when the drive sleeve is in a distal axial end position relative to the actuator.

This is a simple and reliable solution to the fact that the drive sleeve will have to rotate on the unidirectionally rotatable hollow drive rod during release, i.e. when the release button is in its inactive state and the actuator and the drive sleeve assume their distal end positions, while the actuator itself may be perform this movement linearly.

In accordance with an embodiment of the medicament delivery device according to the invention, the coupling means between the drive sleeve and the actuator comprises a tooth coupling provided on an inside surface of a distal end of the actuator.

Other solutions are obviously imaginable, such as providing the surfaces with sand paper-like properties or other friction-enhancing means.

In accordance with an embodiment of the medicament delivery device according to the invention, a pitch of the tooth coupling between the drive sleeve and the actuator is the same or less than a pitch of the threaded connection between the drive sleeve and the hollow drive rod.

This ensures that the tooth coupling between the drive sleeve and the actuator do not connect "one tooth too early" which would reduce the contact surface between the drive sleeve and the actuator. Using a pitch of the tooth coupling which is larger than the pitch of the threaded connection between the drive sleeve and the hollow drive rod will not bring any advantages since the maximal linear contact surface between the teeth will be defined by the pitch of the treaded connection between the drive sleeve and the hollow drive rod anyway.

In accordance with an embodiment of the medicament delivery device according to the invention, the proximal end position of the actuator is defined by the axial position of the rear housing such that by adjusting the relative axial position of the front housing with regard to the rear housing the length of stroke between the distal end position of the actuator and the proximal end position of the actuator is determined, thereby enabling setting of a required medicament delivery dose.

The medicament delivery device according to the present invention has the advantage that a user who normally injects the same dose each time does not have to set the required dose before each injection. The dose is directly dependent on the stroke length of the actuator between the distal end position and the proximal end position and this stroke length is set by adjusting the position of the front housing and the rear housing relative to each other. Once this is done, the actuator will assume its distal end position as soon as the release button is brought to its inactive state and the dose set before the previous injection will automatically be set again.

In accordance with an embodiment of the medicament delivery device according to the invention, the first and second biasing members comprise compression springs.

In accordance with an embodiment of the medicament delivery device according to the invention, the first biasing member comprises a compression spring and the second biasing member comprises a torsion spring.

By providing a torsion spring as the second biasing means, the rotational release of the drive sleeve is facilitated and improved.

In accordance with an embodiment of the medicament delivery device according to the invention, a container holder is arranged at the front housing to receive and hold the medicament container.

In accordance with an embodiment of the medicament delivery device according to the invention, the release button comprises a snap catch element which in the active state of the release button interacts with the locking ring thereby providing the unidirectional rotational movement of the locking ring relative to the rear housing and which generates a click sound during said rotational movement.

The provision of a snap catch element ensures a reliable unidirectional function and the click sound provides an audible and even a tactile feedback which is highly appreciated by many users.

In accordance with an embodiment of the medicament delivery device according to the invention, the actuator is connected to said front housing through guide means and to said rear housing through the locking ring such that the actuator is rotatably locked but axially movable in relation to said front and rear housings when the release button is in its active state.

The locking ring which, when the release button is in its active position, is unidirectionally rotatable relative to the rear housing will allow the actuator to be depressed, i.e. to be axially moved towards its proximal position while the ring rotates on the outer threads of the actuator and the guide means allow the actuator to move axially with respect to the front housing, thus providing reliable function of the medicament delivery device of the present invention. When the release button is in the inactive position, the locking ring is bidirectionally rotatable, thus allowing the actuator to move distally under influence of the first biasing member while the ring rotates in the opposite direction on the outer threads of the actuator.

In accordance with an embodiment of the medicament delivery device according to the invention, the medicament delivery device is a pen-injector. The device according to the present invention is especially suitable when used as a pen injector.

BRIEF DESCRIPTION OF THE DRAWINGS

The invention will now be described in more detail and with reference to the appended drawings in which.

DESCRIPTION OF PREFERRED EMBODIMENTS

Figure 1:
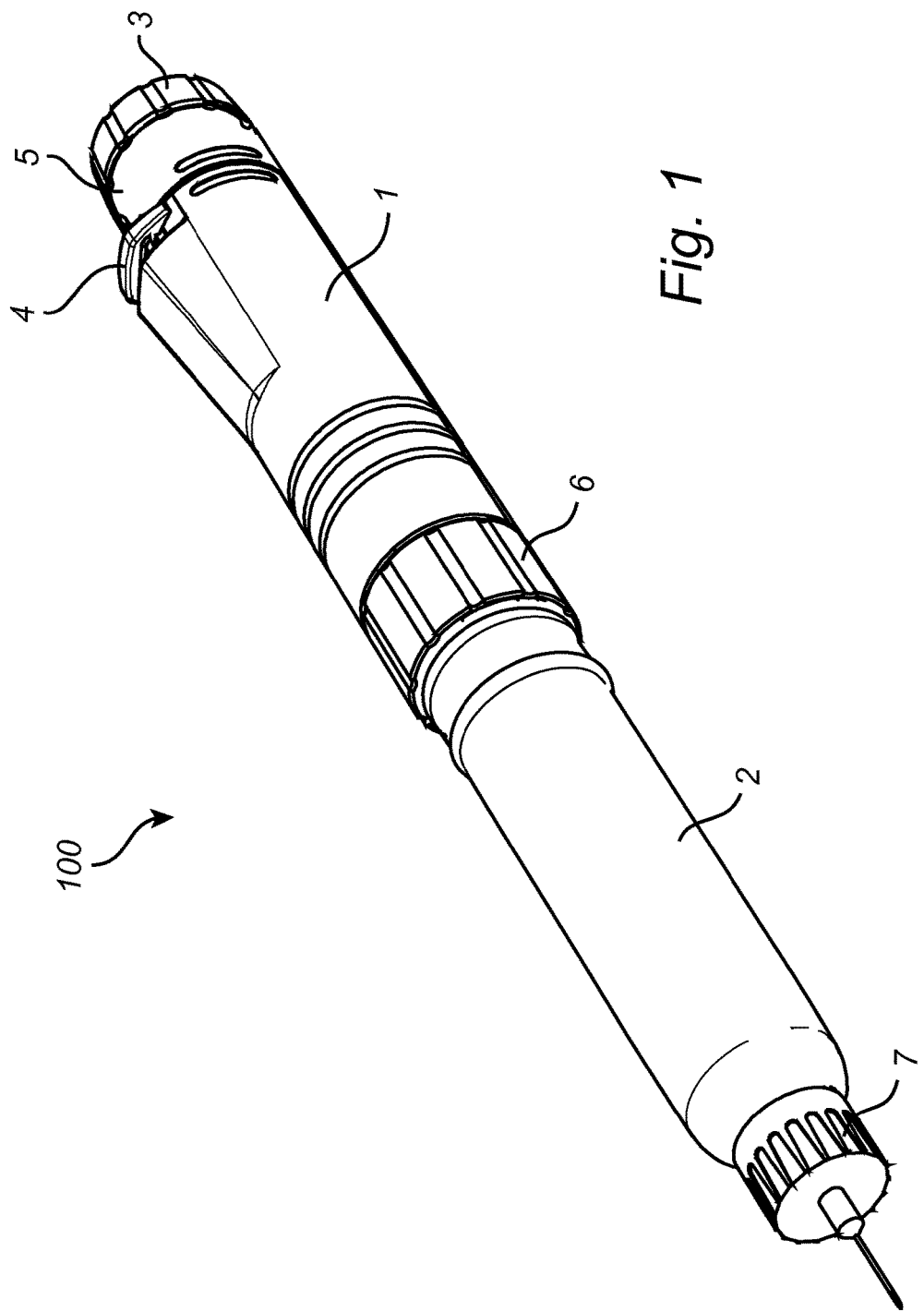
FIG. 1 is a schematic perspective view of an embodiment of the medicament delivery device according to the invention.

In a first embodiment of a medicament delivery device according to the invention, as shown in FIG. 1, a medicament delivery device 100 comprises a rear housing 1 made from e.g. thermoplastic and a container holder 2. As used herein, the term "container" encompasses all types of containers suitable for injectable liquid composition e.g. cartridges, syringes or the like. Concerning the terms "distal" and "proximal" they refer to points which are further away and closer to the injection site respectively. At a proximal end of the medicament delivery device 100 a pen needle 7 is disclosed. The pen needle 7 is known in the art and can be attached to the container holder 2 by means of any known coupling means, such as a thread. The pen needle 7 can of course also be attached to the container itself. At a distal end of the medicament delivery device 100, an actuator 3 is provided by means of which a defined dose of medicament can be injected. Adjacent the actuator 3, a locking ring 5 is provided, the function of which will be described in detail below. A lock sleeve arrangement 6 having an internal and an external component is also provided, which lock sleeve arrangement interconnects the container holder 2 with a front housing (not shown in FIG. 1).

Figure 2:
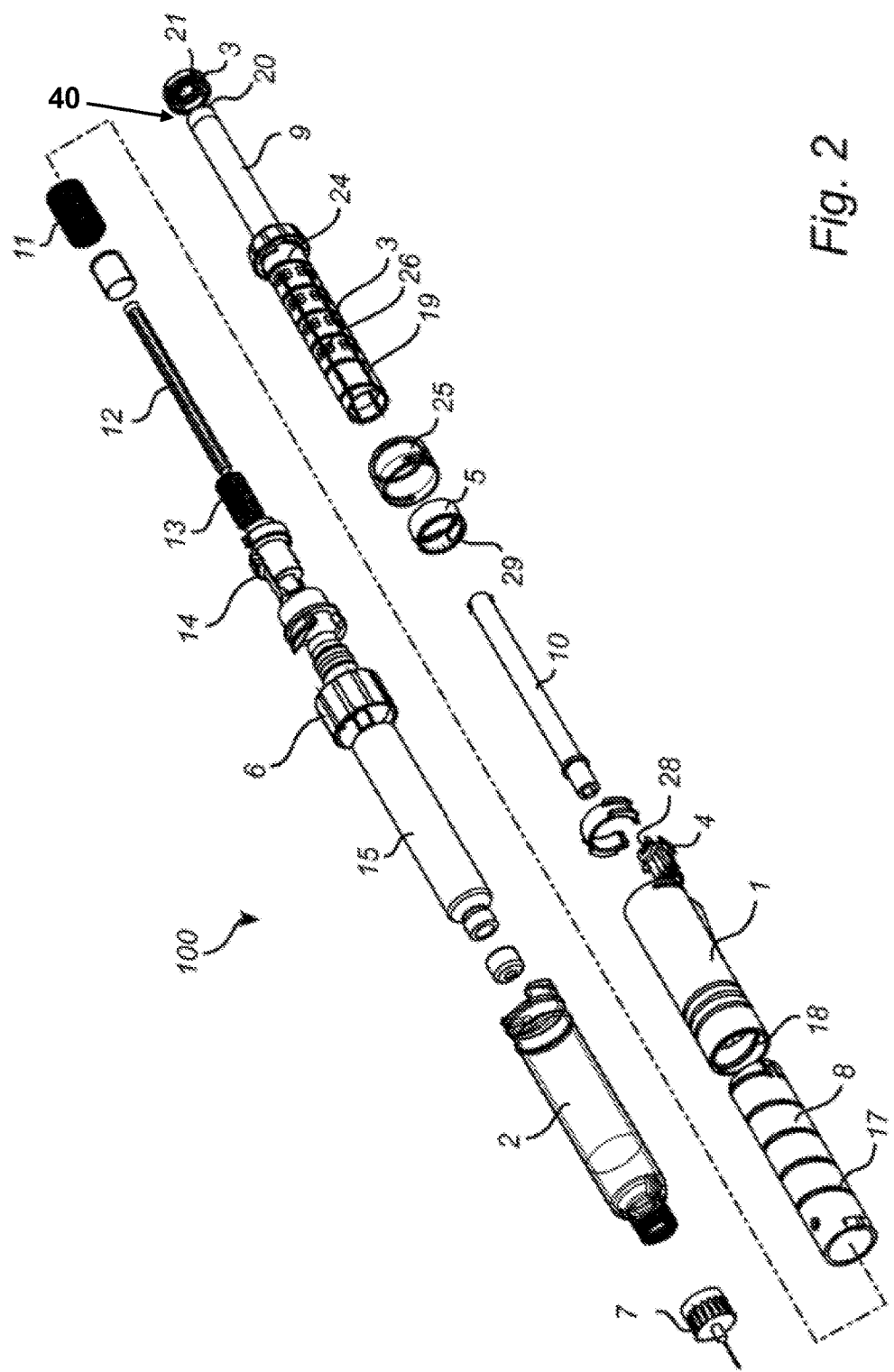
FIG. 2 is a schematic exploded perspective view of an embodiment of the medicament delivery device according to the invention.
Figure 3A:
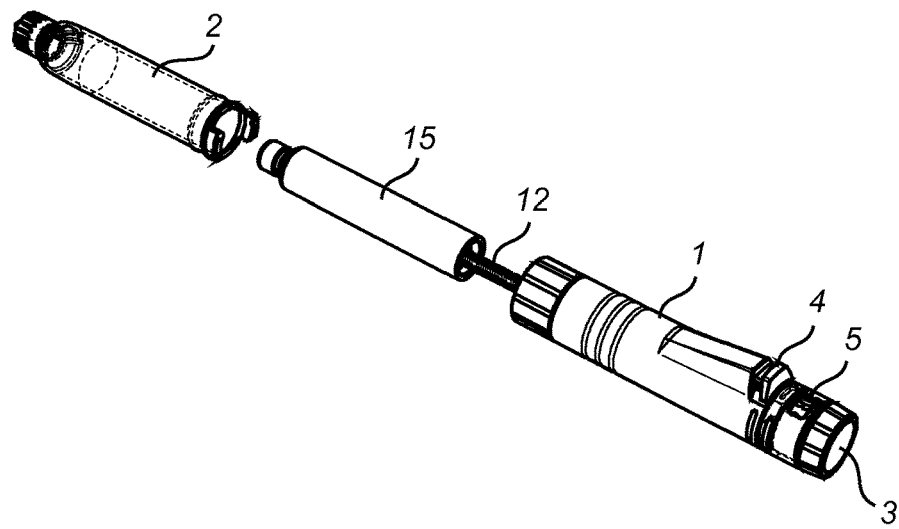
FIGS. 3a-3e are schematic perspective views of different operating modes of an embodiment of the medicament delivery device according to the invention.
Figure 3B:
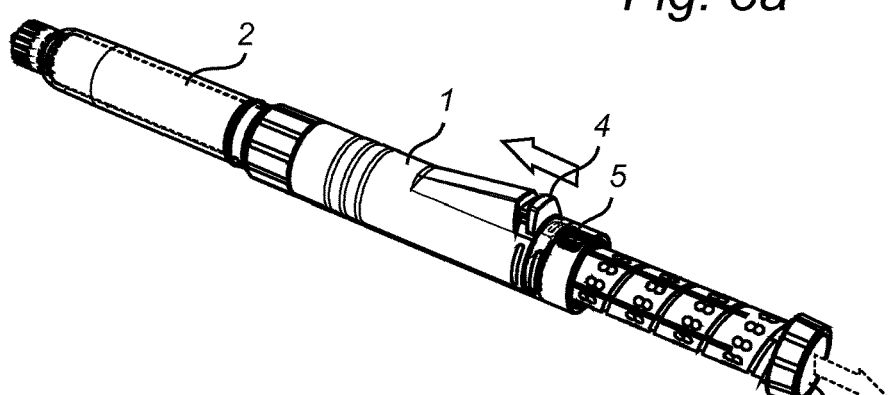
Figure 3C:
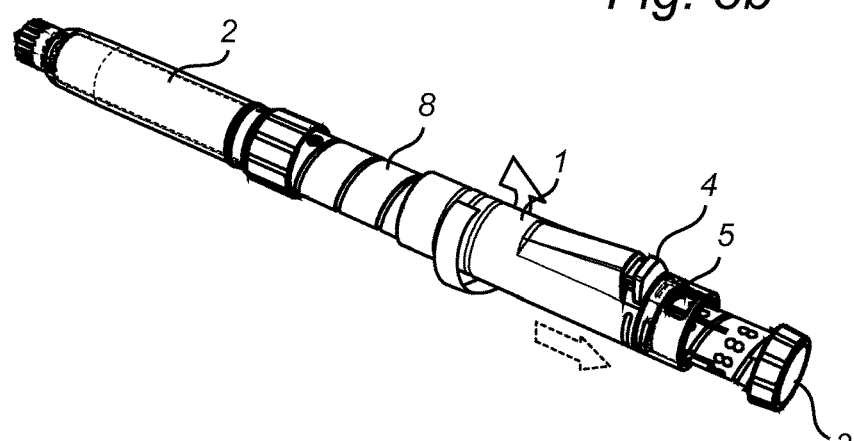
Figure 3D:
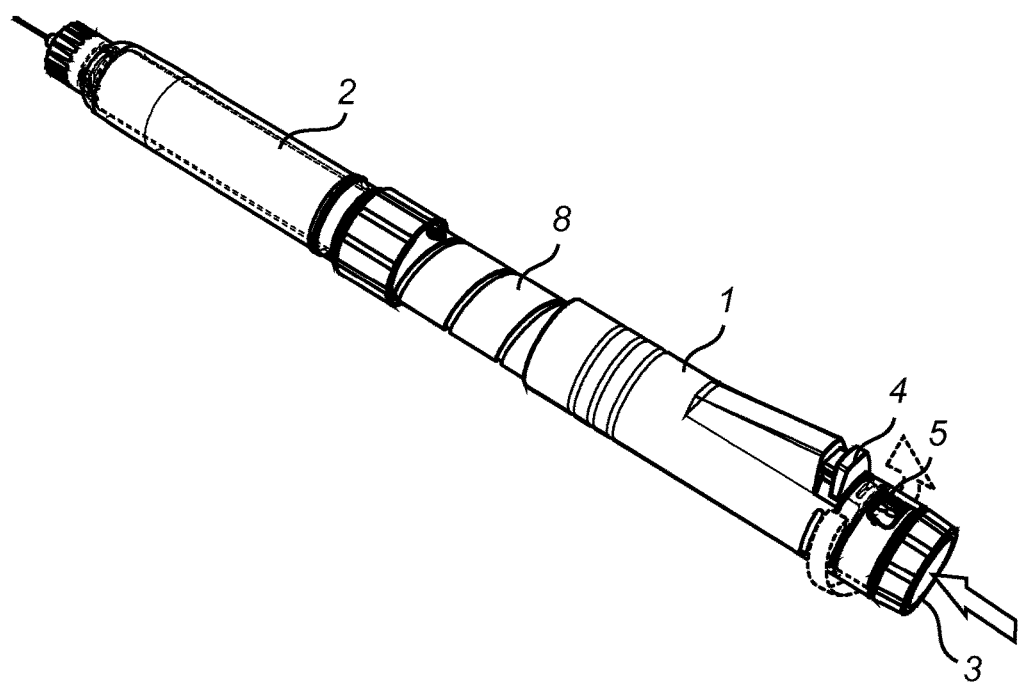
Figure 3E:
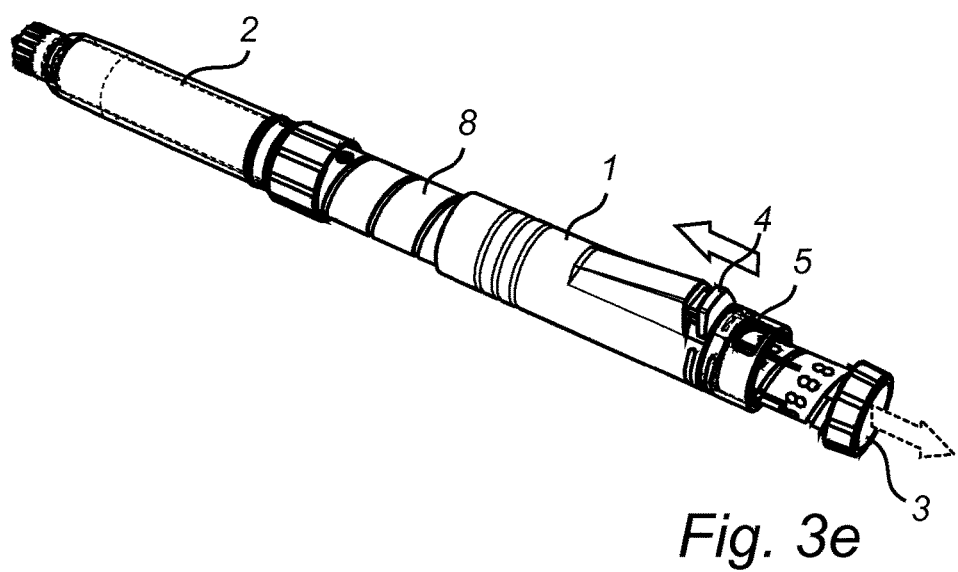
Figure 4:
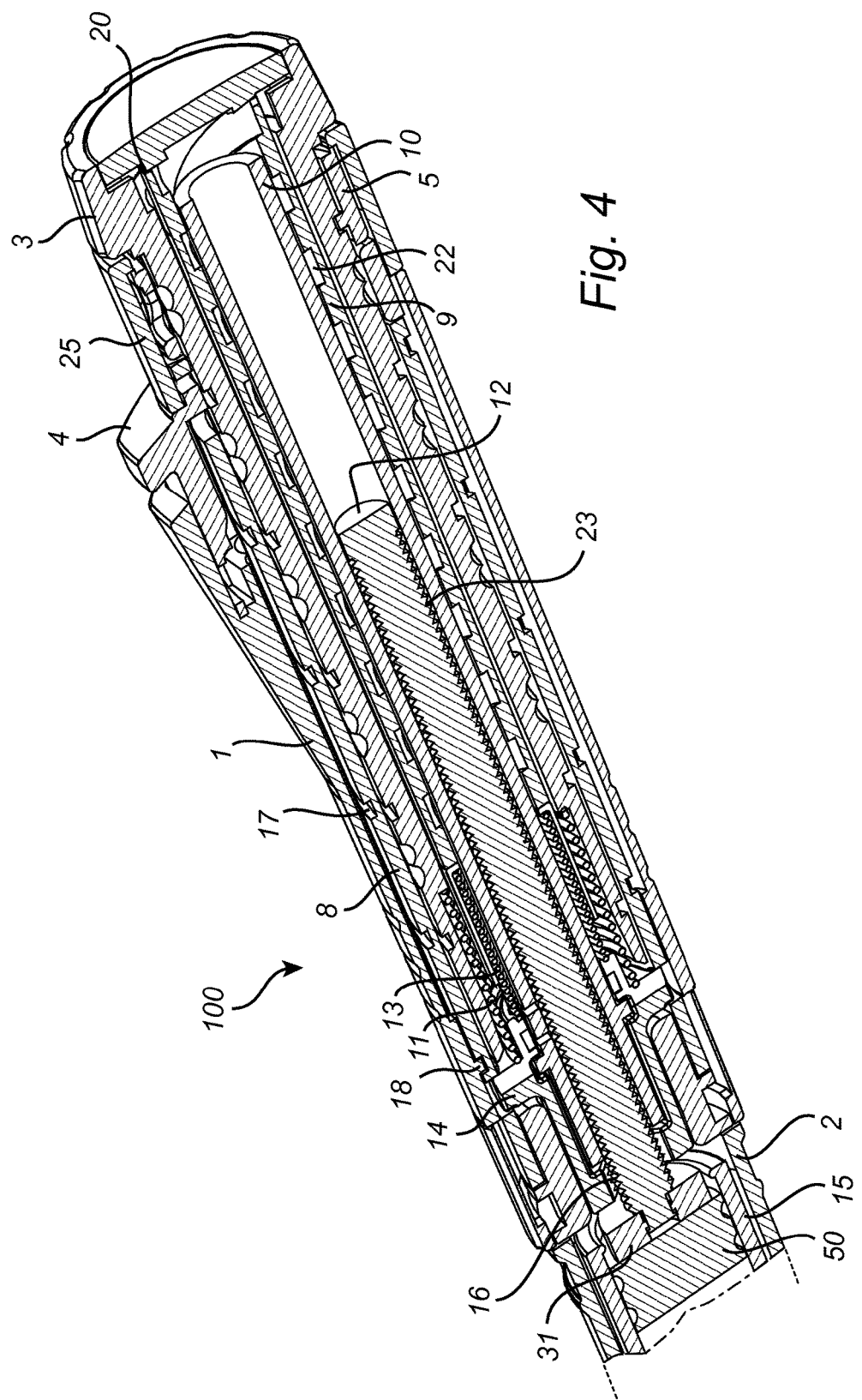
FIG. 4 is a schematic perspective cross-section of an embodiment of the medicament delivery device according to the invention.

The building up of a device 100 of an embodiment of the present invention will now be described, referring mainly to FIGS. 2 and 4 which show the structure of the device. FIG. 2 shows an exploded view of a first embodiment of the medicament delivery device 100 in accordance with the present invention and FIG. 4 shows a cross-sectional view which clearly describes the interaction between the different parts of the medicament delivery device 100. The device comprises a rear, outer housing 1 and a front, inner housing 8 interconnected by means of an outer thread 17 on the front housing 8 and a corresponding inner thread 18 on the rear housing 1. This threaded connection provides a dose setting arrangement for a user of the device 100. This dose setting will be described in detail in relation to FIGS. 3a-3e below. A drive nut 14, which is a split nut or two half nuts, is fixedly arranged at a proximal end of the front housing 8 and an actuator 3 is provided within front and rear housings 1, 8. For illustrative purposes the actuator of FIG. 2 is shown as two components, but in the assembled device they are fixedly attached to each other and act as one component. The actuator 3 is axially, i.e. linearly, movable relative to the rear, outer housing 1 and the front, inner housing 8. Corresponding guiding means 19 are provided in the form of at least one groove on the outer surface of the actuator 3 and a tongue on an inner surface of the front housing 8 (latter not shown in the figures) ensuring relative axial movability while preventing relative rotational movement of the actuator and the front housing 8. A first biasing member 11 in the form of a compression spring is arranged between the actuator 3 and the drive nut 14. The first biasing member 11 biases the actuator 3 towards a distal end position. A drive sleeve 9 is arranged axially and rotationally movable within the actuator 3. However, in a distal end position of the drive sleeve 9, a distal end surface 20 thereof comes into contact with an inner end surface 21 of the actuator 3. The meeting end surfaces 20, 21 are provided with coupling means 40 in the form of teeth that, when in contact with each other, will prevent relative rotational movement of the drive sleeve 9 and the actuator 3. A biasing element in the form of a second biasing member 13 in the form of a compression spring is provided between the drive sleeve 9 and the drive nut 14 in order to force the drive sleeve 9 towards the distal end position, i.e. the position where the drive sleeve abuts the inner surface of actuator 3. A hollow drive rod 10 is arranged within the drive sleeve 9 and they are interconnected by means of an internal thread 22 of the drive sleeve and a corresponding external thread of the hollow drive rod 10 which will convert axial movement of the drive sleeve 9 into rotational movement of the hollow drive rod 10 when the actuator is depressed, thus taking the drive sleeve with it during its axial movement. A proximal end of the hollow drive rod 10 is arranged in the drive nut 14 in such a way that it can only rotate unidirectionally therein. Of course, the hollow drive rod 10 may be connected to other components like to the inner surface of the front housing 8 such that the hollow drive rod 10 can only rotate unidirectionally. Inside the hollow drive rod 10, in turn, a plunger rod 12 is arranged for acting on the plunger 50 of a medicament container. The plunger rod 12 is arranged within the hollow drive rod 10 in such a way that relative axial movement between them is allowed while relative rotational movement is prevented. This is typically done by means of corresponding groove and ridge arrangements on the outer surface of the plunger rod 12 and the inner surface of the hollow drive rod 10 respectively. Preferably, the outer surface of the plunger rod 12 is provided with a groove and the inner surface of the hollow drive rod 10 is provided with a matching ridge extending into the groove thus preventing relative rotational movement while allowing relative axial movement. An outer surface of the plunger rod 12 is provided with threads 23 which are in threaded connection with inner threads 16 of a through-bore in the drive nut 14 which is fixedly arranged at a proximal end of the front housing 8. When the actuator 3 is depressed from a distal position towards a proximal end position the end surfaces 20, 21 comes into engagement and the actuator 3 brings the drive sleeve 9 with it in the axial movement. The inner thread 22 of drive sleeve 9 interacts with the outer thread of the hollow drive rod 10 which is brought into rotational movement. The rotational movement of the hollow drive rod 10 is transferred to the plunger rod 12 and since the plunger rod 12 is in threaded connection with the drive nut 14 this rotational movement will cause the plunger rod 12 to perform an axial movement as well thus forcing the plunger 50 of the medicament container forward such that a medicament is expelled from the device. The plunger rod 12 is provided with a rotatable spinner 31 at its proximal end in order to reduce friction between the rubber plunger 50 and the rotating plunger rod 12. The provision of this drive mechanism provides for a compact construction with excellent possibilities of achieving suitable gear ratios for user friendly pressing power vs. length of stroke and the amount of medicament to be expelled during use.

Previously known devices, such as the one described in WO-2004/002556 have the drawback that the actuator, when released, immediately returns to its initial position, i.e. the distal end position. This means that if the user, for some reason, releases the actuator before the complete dose has been expelled it will be hard, or even impossible to determine how large the injected amount was and how much has to be injected subsequently to arrive at the intended dose. The device 100 of the present invention therefore suggests the provision of a release button 4 and a locking ring 5 arranged on the rear housing 1. The locking ring 5 is provided with an inner thread interconnected with an outer thread 24 on an outer surface of the actuator 3. The locking ring 5 is prevented from axial movement by means of a locking ring cover 25 arranged at the rear housing 1 and is in threaded connection with an outer surface of the actuator 3 such that the locking ring is rotatable relative to the actuator 3 but is prevented from axial movement relative to the rear housing 1 by means of the locking ring cover 25 attached to a rear part of the rear housing 1. The release button 4 is movable between an inactive position and an active position. In the active position the release button 4 interacts with the locking ring 5 such that the locking ring can be unidirectionally rotated only, i.e. allowed to rotate in one direction and prevented from rotation in the other direction. This can be achieved by means of a snap catch 28 element which in the active state of the release button 4 interacts with teeth 29 provided at the locking ring 5 thereby providing the unidirectional rotational movement of the locking ring 5 relative to the rear housing and which generates a click sound during said rotational movement thus providing an audible and even tactile feedback to a user. During depression of the actuator 3 the axial movement thereof will generate a rotational movement of the locking ring riding on the outer thread 24 of the actuator 3. This rotational movement is allowed by the release button 4 but should the user, for some reason, let go of the actuator 3 the release button 4 and the locking ring 5 will prevent the first biasing member 11 from forcing the actuator 3 towards its distal end position. This since rotation of the locking ring 5 is prevented and since the actuator 3 can only move axially under rotation of the locking ring 5 due to their threaded connection, the actuator 3 will remain in its current position if released. If a user, however, moves the release button 4 to its inactive state, the locking ring 5 is free to rotate in both directions and the actuator 3 and the drive sleeve 9 will assume their distal end positions forced by the respective first and second biasing members 11, 13. It should be noted that the second biasing member 13 could comprise a torsion spring instead of a compression spring or a combination thereof i.e. a helical spring that can be compressed and twisted. This is especially suitable since the drive sleeve will perform a rotational movement riding on the threads of the hollow drive rod 10 when the release button 4 is in the inactive state. The hollow drive rod 10 being unidirectionally mounted in the drive nut 14 will force the drive sleeve 9 to rotate while the drive rod 10 remains stationary and the second biasing member 13 will facilitate this movement. When released, the actuator 3 will very quickly return to its distal end position while the drive sleeve 9, having to perform a combined axial and rotational movement, will return to the distal end position to connect with the inner end surface 21 of the actuator 3 somewhat later, i.e. with a delay. The toothed coupling 40 between the drive sleeve 9 and the actuator 3 preferably has the same or a smaller pitch than the threaded connection between the drive sleeve 9 and the hollow drive rod 10.

Figure 5:
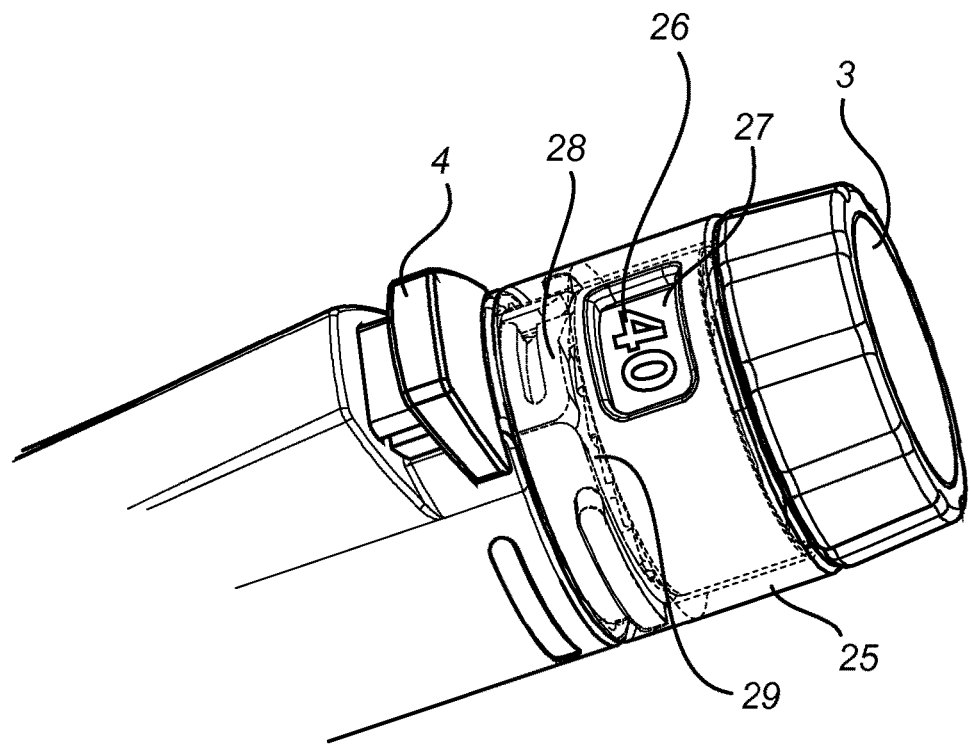
FIG. 5 is a schematic perspective view of a detail of the medicament delivery device according to the invention.

The function of the device 100 according to the invention will now be described referring to FIGS. 3a-3e. When a used, emptied container is to be replaced, the container holder 2 is twisted 90 degrees around its longitudinal axis and can thereafter be removed. This twisting also opens the drive nut 14 due to the elliptical and angled shape of the internal component of the lock sleeve arrangement 6. This function is described in the prior art document EP-0554996B1 to which reference is made. The opening of the drive nut 14 allows the user to press the plunger rod 12 towards a distal end position and push a new, full container 15 onto the plunger rod 12 (FIG. 3a). Typically, 3 ml containers will be used. When this is done, the container holder 2 is again locked to the device 100 by twisting it 90 degrees in the opposite direction. In a next step the release button 4 is brought to its inactive state which will cause the actuator 3 and the drive sleeve 9 to return to their distal end positions biased by the first and second biasing member 11, 13 (FIG. 3b). Thereafter, a required dose is set by adjusting the relative axial position of the rear housing 1 and the front housing 8 by screwing them in or out until a preferred dose has been set (FIG. 3c). Since the distal end position of the actuator 3 is always the same defined by the guiding means in the front housing 8 and the proximal end position of the actuator 3 is defined by the rear housing 1, the relative axial position of the front housing 8 with regard to the rear housing 1 determines the length of stroke of the actuator 3, which in turn corresponds to a set dose. The pitch of the threaded connection between the rear housing 1 and the front housing 8 corresponds to that between the actuator 3 and the locking ring 5. Therefore, the locking ring 5 will follow any rotational movement of the rear housing 1 during setting of a dose. The actuator 3 is rotatably locked relative to the front housing 8. The actuator 3 is provided with dose indications 26 on the outer surface thereof. These dose indications are visible through a dose window 27 in the locking ring 5 and since the locking ring cover 25 is transparent, this window is visible at all time. See in this respect also FIG. 5. Unlike some prior art devices, where a dose set too high cannot be made undone, a user of a device 100 according to present invention can adjust the dose upwards and downwards until a required dose has been set. This makes the device 100 according to the present invention more user friendly and cost-effective. This since a dose set too high in a prior art device had to be discarded and a new, correct dose be set before injection could be done.

A flexing bump in the front housing 8 snaps on the inner surface of the rear housing 1, thus giving a tactile indication to the user for each dose increment. This also prevents the rear housing 1 from rotating relative to the front housing 8 during injection. As soon as the user has set a required dose, which can readily be seen in the dose window, a needle is attached and the medicament can be injected (FIG. 3d). If the injection is halted at any point the locking ring 5 and the actuator 3 will stop at that position, with the remaining part of dose showing in the dose window. The user therefore has complete control of the injection process all the time. When a user is ready to inject another dose, the release button 4 is brought to its inactive position and the actuator 3 will return to its distal end position. If the user intends to inject the same dose as the last time, no dose has to be set since the last dose is still set by the relative position of the rear housing 1 and front housing 8 i.e. an automatic dose memory.

Finally, it is realized, that a medicament delivery device according to the invention has a number of advantages over the known prior art devices. Due to the fact that the device has a completely mechanical design, reliability can be ensured at all time without being dependent on batteries or similar. The actuator 3 will not automatically return to its distal end position when released. The set dose will not have to be reset for each injection occasion; instead the device according to the present invention provides an automatic dose memory. It is re-usable and the user can change the emptied container to a new container in a simple manner. The device allows for a variable dose size and the setting of the dose can be set downwardly and upwardly during the dose setting until a required dose has been set. The set dose is shown in the dose window 27 and during injection the remaining dose to be injected is always shown in a countdown manner. The fact that the remaining amount of the dose to be delivered is always shown in the dose window 27 gives the device according to the present invention another great advantage over prior art devices. If the container should be emptied during an ongoing injection, i.e. there was not enough medicament in the container, the user just reads the dose indication 26 in the dose window 27 and thereafter a new container is loaded and the remaining dose can be set and injected, thus arriving at the required total dose.

It is to be understood that the embodiments described above and in the drawings are to be regarded only as non-limiting examples of the invention and that they may be modified in many ways within the scope of the claims.

The invention claimed is:

1. A medicament delivery device having a proximal end and a distal end, the medicament delivery device comprising:
   a front housing and a rear housing interconnected and axially displaceable relative to each other between an extended position and a retracted position, wherein an axial displacement of the front housing relative to the rear housing sets a dose to be delivered;
   a plunger rod configured to act on a plunger of a medicament container;
   a drive mechanism configured to drive the plunger rod;
   an actuator operably connected to each of the front and rear housings and axially movable in the front and rear housings between a proximal end position and a distal end position, wherein the actuator is biassed by a first biassing element toward the distal end position;
   a drive sleeve releasably connected to the actuator and configured to act on the drive mechanism to drive the plunger rod;
   a locking ring rotatably arranged at a distal end of the rear housing and in threaded connection with an outer surface of the actuator, wherein the locking ring is prevented from axial movement relative to the rear housing; and
   a release button movably disposed on the rear housing between an active state and an inactive state, wherein the release button in the active state allows unidirectional rotational movement of the locking ring relative to the rear housing such that the actuator is axially movable toward the proximal end position by rotational movement of the locking ring, and the release button in the inactive state allows bidirectional rotational movement of the locking ring relative to the rear housing such that the actuator is axially movable toward the proximal end position or the distal end position by rotational movement of the locking ring.

2. The medicament delivery device of claim 1, wherein the front and rear housings are interconnected and axially displaceable relative to each other through an outer thread on the front housing and an inner thread on the rear housing.

3. The medicament delivery device of claim 1, wherein the drive sleeve is biassed toward the distal end of the medicament delivery device by a second biassing element.

4. The medicament delivery device of claim 3, wherein the first and second biassing elements include compression springs.

5. The medicament delivery device of claim 3, wherein the first biassing element comprises a compression spring, and the second biassing element comprises a torsion spring.

6. The medicament delivery device of claim 1, wherein the outer surface of the actuator includes dose indicators, and the locking ring has a dose window through which the dose indicators are visible.

7. The medicament delivery device of claim 1, further comprising a transparent locking ring cover configured to hold the locking ring axially immovable relative to the rear housing.

8. The medicament delivery device of claim 1, wherein the drive mechanism comprises:
   a drive nut fixedly arranged near a proximal end of the front housing, the drive nut comprising a through bore, and a part of the bore having an inner thread; and
   a hollow drive rod having an outer thread, wherein a proximal end of the hollow drive rod is unidirectionally rotatably mounted to the drive nut;
   wherein the plunger rod is arranged within the hollow drive rod and in threaded connection with the inner thread of the bore, the plunger rod and the hollow drive rod are configured to mate with each other such that axial movement of the plunger rod relative to the hollow drive rod is allowed and rotation of the plunger rod relative to the hollow drive rod is prevented, and the drive sleeve is arranged in threaded connection with the outer thread of the hollow drive rod.

9. The medicament delivery device of claim 8, wherein the drive sleeve is arranged within and axially movable relative to the actuator, and the device further comprises a coupler configured to prevent the drive sleeve and actuator from rotational movement relative to each other when the drive sleeve is in a distal axial end position relative to the actuator.

10. The medicament delivery device of claim 9, wherein the coupler comprises a tooth coupling provided on an inside surface of a distal end of the actuator.

11. The medicament delivery device of claim 10, wherein a pitch of the tooth coupling is the same or less than a pitch of the threaded connection between the drive sleeve and the hollow drive rod.

12. The medicament delivery device of claim 1, wherein the proximal end position of the actuator is defined by an axial position of the rear housing such that by adjusting a relative axial position of the front housing relative to the rear housing, a length of stroke between the distal and proximal end positions of the actuator is determined, thereby enabling setting of a medicament dose.

13. The medicament delivery device of claim 1, further comprising a container holder arranged at the front housing and configured to receive and hold the medicament container.

14. The medicament delivery device of claim 1, wherein the release button comprises a snap catch element; the release button in the active state interacts with the locking ring, thereby providing the unidirectional rotational movement of the locking ring relative to the rear housing; and the snap catch element generates a click sound during the rotational movement.

15. The medicament delivery device of claim 1, wherein the actuator is connected to the front housing by a guide and to the rear housing by the locking ring such that the actuator is rotatably locked but axially movable relative to the front and rear housings when the release button is in the active state.

16. The medicament delivery device of claim 1, wherein the medicament delivery device is a pen-injector.

* * * * *